(12) United States Patent
Justino et al.

(10) Patent No.: US 7,538,139 B2
(45) Date of Patent: May 26, 2009

(54) SUGAR DERIVATIVES COMPRISING OXIRANES OR α, β-UNSATURATED γ-LACTONES, PROCESS FOR THEIR PREPARATION AND THEIR UTILISATION AS PESTICIDES

(75) Inventors: Jorge Alberto Guerra Justino, Santarem (PT); Amélia Pilar Grases Santos Silva Rauter, Lisbon (PT); Tana Lukeba Canda, Luanda (AO); Richard Wilkins, Tyne and Wear (GB)

(73) Assignees: Instituto Politecnico De Santarem/Escola Superior Agraria, Santarem (PT); Faculdade de Ciencias da Universidade de Lisboa, Lisboa (PT); University of Newcastle, Newcastle upon Tyne (GB)

( * ) Notice: Subject to any disclaimer, the term of this patent is extended or adjusted under 35 U.S.C. 154(b) by 122 days.

(21) Appl. No.: 11/494,865

(22) Filed: Jul. 28, 2006

(65) Prior Publication Data
US 2007/0117865 A1 May 24, 2007

Related U.S. Application Data

(63) Continuation-in-part of application No. 10/902,970, filed on Jul. 30, 2004, now abandoned.

(51) Int. Cl.
*A01N 43/08* (2006.01)
(52) U.S. Cl. ...................................... 514/473
(58) Field of Classification Search ............... 549/263, 549/295, 320; 514/449, 461, 473
See application file for complete search history.

(56) References Cited

FOREIGN PATENT DOCUMENTS

EP      1464649      *   8/2003

OTHER PUBLICATIONS

Just et al., Canadian journal of chemistry, 1980, vol. 58, pp. 1799-1805.*
Ghosh et al., Tetrahedron Letters, vol. 39, pp. 4651-4654.*
Brownbridge, P.; Chan, T. H., "Chemistry of 2,5-bis(trimethylsiloxy)furans.[1] III: synthesis of γ-hydroxybutenolides." *Tetrahedron Lett.* 1980, 21, pp. 3431-3434.
Cafieri, F; Fattorusso, E.; Santacroce, C; Minale, L.; "Fasciculatin, a novel sesterterpene from the sponge *Ircinia fasciculata*", *Tetrahedron* 1972, vol. 28, pp. 1579-1583.
Cardellach, J.; Estopa, C.; Font, J.; Moreno-Manas, M.; Ortuno, R. M.; Sanchez-Ferrando, F.; Valle, S.; Vilamajo, L., "Studies on structurally simple α,β-butenolides-I: new syntheses of racemic γ-hydroxylmethyl-α,β-butenolide and derivatives", *Tetrahedron* 1982, vol. 38, No. 15, pp. 2377-2394.
Choudhury, P. K.; Foubelo, F.; Yus, M., "Direct indium-promoted preparation of α-methylene-γ-lactones from 2-(bromomethyl)-acrylic acid and carbonyl coumpounds", *Tetrahedron* 55 (1999), pp. 10779-10788.

Cimino, G.; De Stefano, S.; Guerriero, A.; Minale, L., "Furanosesquiterpenoids in sponges-I: Pallescensin-1, -2, and -3 from *Disidea pallescens*", *Tetrahedron Lett.* 1975, No. 17, pp. 1417-1420.
Cimino, G.; De Stefano, S.; Minale, L.; Fattorusso, E., "Ircinin-1 and -2 linear sesterterpenes from the marine sponge *Ircinia oros*", *Tetrahedron* 1972, vol. 28, pp. 333-341.
Csuk, R.; Furstner, A.; Weidmann, H., "Efficient, low temperature reformatsky reaction of extended scope", *J. Chem. Soc. Chem. Commun.* 1986, p. 775.
Csuk, R.; Glanzer, B. I.; Hu, Z.; Boese, R., "Double stereodifferentiating dreiding-schmidt reactions", *Tetrahedron* 1994, Vo. 50, No. 4, pp. 1111-1124.
Dax, K.; Rauter, A. P.; Stutz, A. E.; Weidmann, H., "Enfache synthesen von 5-desoxy-hexofuranurono-6-3-lactonen", *Liebigs Ann. Chem.* 1981, pp. 1768-1773. English Abstract (Reactions of D-glucuronic acid, XV, facile synthesis of 5-deoxy-hexofuranurono-6,3-lactones).

(Continued)

*Primary Examiner*—D. Margaret Seaman
*Assistant Examiner*—Niloofar Rahmani
(74) *Attorney, Agent, or Firm*—Merchant & Gould P.C.

(57) ABSTRACT

A method for controlling pests, the method comprising applying an effective amount to pests or their locus of one or more compounds of general formula (I)

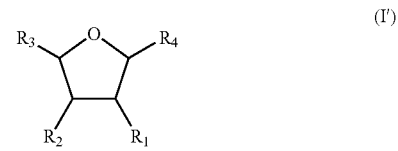

(I')

wherein $R_1$ and $R_2$ represent, independently from each other, hydrogen, halogen, alkoxy, substituted alkoxy or an ester group; $R_1$ and $R_2$, together with the carbon atoms to which they are attached, represent an oxirane ring; $R_1$ and $R_2$, taken together, represent an akylidenedioxy or substituted alkylidenedioxy group; and $R_3$ represents —$CH_2R_6$, wherein $R_6$ represents an ester group, oxiranyl, or a group of formula

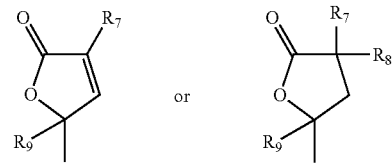

wherein $R_7$ represents hydrogen or alkyl, $R_8$ represents phenylsulfanyl, phenylselenyl, phenylsulfoxy or phenylselenoxy, and $R_9$ represents hydrogen, ethoxycarbonyl or carbamoyl; and $R_4$ represents, independently, hydrogen, alkoxy or substituted alkoxy, or $R_1$ and $R_4$, taken together, represent an alkylidenedioxy or a substituted alkylidenedioxy group; wherein the pest dies as a result of contact with the compound.

29 Claims, No Drawings

OTHER PUBLICATIONS

Devon, T. K.; Scott, A. I., "Terpenes", *Handbook of Naturally Occurring Compounds*; Academic Press: New York, 1972; vol. II, pp. 79-175.

Faulkner, D. J. ariabilin, an antibiotic from the sponge, *Ircinia variablis*, Tetrahedron Lett. 1973, No. 39, pp. 3821-3822.

Figueredo, M.; Font, J.; Virgili, A., "Studies on structurally simples α,β-butenolides. VII. an easy entry to γ-thiomethyl- and γ-aminomethyl-α,β-butenolides", Tetrahedron 1987, vol. 43, No. 8, pp. 1881-1886.

Finney, D. J., "4.7 Fiducial limits", *Probit Analysis*, 1971, 3rd Ed., Cambridge University Press, London, p. 76-80.

Garem, B., "Tetrahedron report number 59, from glucose to aromatics: recent developments in natural products of shikimic acid pathway", Tetrahedron 1978, vol. 34, pp. 3353-3383.

Gutshe, C. D., "The reaction of diazomethane and its derivatives with aldehydes and ketones", *Organic Reactions*, New York: John Wiley & Sons, Inc., 1954, vol. VIII, 364-429.

Hanessian, S.; Girard, C., "Double stereodifferentiating dreiding-schmidt reactions", Synlett 1994, 10, pp. 865-867.

Haynes, L. J.; Plimmer, J. R, "Tetronic Acids", *Quarterly Reviews*, London: The Chemical Society, 1960, vol. XIV, No. 3, Chapter 14, pp. 292-315.

Klein Gebbinck, E. A.; Stork, G. A.; Jansen, B. J. M.; of Groot, A., "Synthesis and insect antifeedant activity of 2-substituted 2,3-Dihydrofuran-3-ols and butenolides (Part II)", Tetrahedron 55 (1999), pp. 11077-11094.

Kotora, M.; Negishi, E., "Highly efficient and selective procedures for the synthesis of γ-alkylidenbutenolides via palladium-catalyzed ene-yne coupling and palladium- or silver-catalyzed lactonization of (Z)-2-En-4-moic acids. Synthesis of rubrolides A, C, D, and E." Synthesis 1997, pp. 121-128.

Kwart, H.; Hoffmann, D. M., "Observations regarding the mechanism of olefin epoxidation with per acids", J. Org. Chem. 1966, vol. 31, pp. 419-425.

Larock, R. C.; Riefling, B.; Fellows, C. A. J."Mercury in organic Chemistry. 12.[1] Synthesis of β-chloro-$\Delta^{\alpha,\beta}$-butenolides via mercuration-carbonylation of propargylic alcohols[2]", J. Org. Chem. 1978, vol. 43, No.1, pp. 131-137.

Ma, S.; Schi, Z.; Yu, Z. "Synthesis of β-halobutenolides and the Pd(0)-catalyzed cross-coupling reactions with terminal alkynes and organozinc reagents. A general rout to β-substituted butenolides and formal synthesis of *cis*-whisky lactone" Tetrahedron 55 (1999), pp. 12137-12148.

Marshall, P. G., "Steroids: Cardiotonic Glycosides and Aglycons; Toad Poisons", *Rodd's Chemistry of Carbon Compounds, Second Edition*; Rodd, E. H., Ed.; Elsevier: New York, 1970; vol. II Part D, Chapter 17, pp. 360-421.

Mitsunobu, O., "The use of diethyl azodicarboxylate and triphenylphosphine in synthesis and transformation of natural products", Synthesis 1981, pp. 1-28.

Newth, F. H.., "The O-toluene-p-sulphonyl derivatives of 1,5-anhydro-4,6-O-benzylidene-D-glucitol", J. Chem. Soc. 1959, 2717-2720.

Rao, A. S., "Tetrahedron report number 150, recent advances in the preparation and synthetic applications of oxiranes", Tetrahedron 1983, vol. 39, No. 14, pp. 2323-2367.

Rauter, A. P.; Ferreira, M. J.; Font, J.; Virgili, A.; Figueredo, M.; Figueiredo, J. A.; Ismael, M. I.; Canda, T. L., "Synthetic, fungicidal unsaturated-γ-lactones attached to furanosidic systems. Configurational determination by nuclear overhauser effect", J. Carbohydr. Chem. 1995, 14(7), pp. 929-948.

Rauter, A. P.; Figueiredo, J. A.; Ismael, M. I., "Synthesis of pseudo-C-nucleosides", Carbohydate. Research, 1989, 188, pp. 19-24.

Rauter, A. P.; Figueiredo, J. A.; Ismael, M. I.; Pais, M. S.; Gonzalez, A. G.; Dias, J.; Barrera, J. B., "Synthesis of α-methylene-γ-lactones infuranosidic systems", J. Carbohydr. Chem. 1987, 6(2), pp. 259-272.

Rauter, A. P.; Figueiredo, J.; Ismael, M.; Canda, T. L.; Font, J.; Figueredo, M., "Efficient synthesis of α,β-unsaturated g-lactones linked to sugars", Tetrahedron: Asymmetry 2001, 12, pp. 1131-1146.

Robertson, J. L.; Preisher, H., *Pesticide Bioassays with Arthropods*, 1992, CRC Press, Boca Raton, FL, pp. 1-127.

Rodrigues, J.; Dulcere, J. P., "Cohalogenation in organic synthesis", Synthesis, 1993, pp. 1177-1202.

Rothberg, I.; Shubiak, P., "The structure of some antibiotics from the sponge *Ircinia strobilina*", Tetrahedron Lett. 1975, No. 10, pp. 769-722.

Schmitz, F. J.; Kraus, K. W.; Ciereszko, L. S.; Sifford, D.. H.; Weinheimer, A. J.Áncepsenolide: A novel Bisbutenolide of Marine Origin, *The Tetrahedron Letters*, The International Organ for the Rapid Publication of Preliminary Communications in Organic Chemistry, Pergamon Press, Ltd., Printed in Great Britian, 1966, No. 1., pp. 97-104.

Szeja, W., "Phase transfer-catalyzed preparation of oxiranes", Synthesis 1985, pp. 983-985.

Waggins, L. F., "Deamination of certain amino derivatives of sugars and sugar alcohols", Nature, Apr. 8, 1950, vol. 165, p. 566.

Hanessian et al., "Mild and Effect Preparation of γ-Substituted α,β-Unsaturated γ- Butyrolactones from Epoxides", Journal of the Chemical Society Chemical Communications (1986); 10: 754-755.

Rauter et al., "synthesis of Phenylseleno Sugars from Epoxides and of of α, β-Unsaturated Carbonyl Derivatives for the Study of Their Insecticidal Activity," Journal of Carbohydrate Chemistry (2004); 23: 239-251.

Rauter et al. "Efficient synthesis of α, β-Unsaturated γ-lactones linked to sugars," Tetrahedron: Asymmetry, vol. 12, pp. 1131-1146.

Lemee et al. "Synthesis of a Tetrahydrofuran Fragment of Annonaceous Acetogenin from D-Galactal," Tetrahedron Letters, vol. 40, pp. 2761-2764.

Rauter et al. "Synthetic, fungicidal unsaturated γ-lactones attached to furanosidic systems. Configurational determination by nuclear overhauser effect," Journal of Carbohydrate Chemistry, vol. 14, pp. 929-948.

* cited by examiner

SUGAR DERIVATIVES COMPRISING OXIRANES OR α, β-UNSATURATED γ-LACTONES, PROCESS FOR THEIR PREPARATION AND THEIR UTILISATION AS PESTICIDES

This is a Continuation-in-Part of U.S. application Ser. No. 10/902,970, filed Jul. 30, 2004 and which application(s) are incorporated herein.

FIELD OF THE INVENTION

The present invention relates to sugar derivatives comprising oxiranes or α,β-unsaturated γ-lactones with pesticidal, particularly insecticidal, activity, to processes for their preparation and their utilisation as pesticides, which are particularly effective against fruit fly, domestic fly and white fly.

BACKGROUND OF THE INVENTION

Compounds with the α,β-unsaturated γ-lactone moiety in their structure occur in the plant kingdom, as metabolites of lichens and fungi,[1] as sesquiterpene derivatives[2] or as steroid glycosides.[3]

Natural products possessing this structural element are also components of animal species such as sponges.[4]

Many of these compounds exhibit a variety of biologic activities such as antifungal, insecticidal, antibacterial, phytotoxic and anti-inflammatory. Some of them are antibiotics, potential anticancer agents and cyclooxygenase or phospholipase $A_2$ inhibitors.[5]

Due to their biological importance, several synthetic methods have been developed for the preparation of α,β-unsaturated γ-lactones. The synthesis of the endocyclic lactones (α,β-butenolides) is reported in the literature, and includes mercuration-carbonylation of propargylic alcohols,[6] condensation of 2,5-bis(trimethylsiloxy)furans with carbonyl compounds in the presence of titanium tetrachloride[7] and various transformations of $C_3$ synthons, such as, for example, glycidaldehyde.[8]

Other references report methods for the synthesis of γ-alkylidene-α,β-butenolides[9] and for the preparation of α,β-butenolide derivatives with insect antifeedant activity.[10]

A method for the preparation of the exocyclic type lactones involves the reaction of 2-(bromomethyl)acrylic acid in the presence of indium with carbonyl compounds, to give α-methylene-γ-butyrolactones in 7-96% yield.[11]

Previous work reports the synthesis of butenolides through the condensation of sugar epoxides with the dianion of phenylselenoacetic acid, followed by hydrolysis and subsequent oxidation of the intermediate phenylselenolactone.[12,13,14] The nucleophilic opening of the oxirane is stereospecific, the configuration of the stereogenic centre in the final lactone being determined by the centre of chirality of the starting epoxide.

Another method for the synthesis of α,β-unsaturated γ-lactones involves a Reformatsky type reaction of a ketosugar or a dialdofuranose with ethyl bromomethylacrylate and zinc in THF under reflux.[13,14,15]

Ethyl bromomethylacrylate and zinc-silver/graphite at −78° C have been successfully applied to the synthesis of hydroxyesters from cyclic ketones,[16] ketosugars and a 2,3-O-isopropylidene-D-erythronolactone[17] and to the synthesis of α,β-unsaturated γ-lactones from some ketosugars.[16]

The synthesis of 3-ulosonic acids via a samarium iodide Reformatsky reaction of aldonolactones was also reported.[18]

Some of this type of compounds, reported in the literature, have fungicidal efficacy.[13]

Epoxy sugars are versatile intermediates in organic synthesis, due to the ease of their preparation from a variety of starting materials and due to their susceptibility to reactions for example with electrophiles, nucleophiles, acids and bases. Furthermore, epoxides are part of a range of compounds recognised as active principles, with biological and pharmacological activity.[19] Reference can be made for example to cytotoxic metabolites, namely crotepoxide, pipoxide and senepoxide, the latter playing an important role in plants as an antiparasitic agent.[20]

Methods for the preparation of epoxysugars use halohydrins as intermediate compounds,[21] and also aminosugars,[22] tosylates and/or mesylates,[23] vicinal diols,[24,25] glycals[26] and carbonyl compounds.[27]

SUMMARY OF THE INVENTION

This invention is related to methods of pesticidal use of compounds of general formula (I) described further on.

These compounds possess efficacy as insecticides with high toxicity to fruit fly (*Drosophila melanogaster*), house fly (*Musca domestica*) and white fly (*Trialeurodes vaporarium*).

On the other hand the compounds are not toxic to brine shrimps (*Artemia salina*), the reference organisms in assays to evaluate the potential toxicity hazard to organisms in ecosystems.

DETAILED DESCRIPTION OF THE INVENTION

The invention is directed to the use, as pesticides, of a family of compounds of general formula (I):

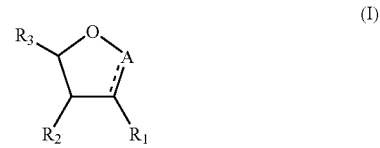

wherein

----- represents a carbon-carbon single or double bond;
-----A----- represents —CH($R_4$)—, if said carbon-carbon bond is a single bond,
  wherein
    $R_4$ represents, independently, hydrogen, alkoxy or substituted alkoxy, or
    $R_1$ and $R_4$, taken together, represent an alkylidenedioxy or substituted alkylidenedioxy group; or
-----A----- represents =C($R_5$)—C(=O)—, if said carbon-carbon bond is a double bond,
  wherein:
    $R_5$ represents hydrogen or halogen;
$R_1$ and $R_2$ represent, independently, hydrogen, halogen, alkoxy, substituted alkoxy or an ester group; or
$R_1$ and $R_2$, together with the carbon atoms to which they are attached, represent an oxirane ring; or
$R_1$ and $R_2$, taken together, represent an akylidenedioxy or substituted alkylidenedioxy group; and
$R_3$ represents —$CH_2R_6$,
  wherein
    $R_6$ represents an ester group, oxiranyl, or a group of formula

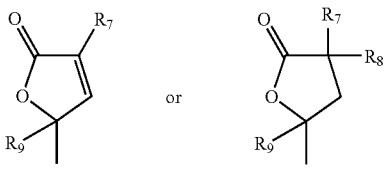

wherein
  $R_7$ represents hydrogen or alkyl,
  $R_8$ represents phenylsulfanyl, phenylselenyl, phenylsulfoxy or phenylselenoxy, and
  $R_9$ represents hydrogen, ethoxycarbonyl or carbamoyl.

In a first embodiment, the invention is directed to methods for use as pesticides, of a subgroup of compounds of the formula (I'):

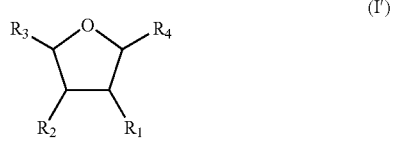

(I')

wherein
  $R_1$ and $R_2$ represent, independently from each other, hydrogen, halogen, alkoxy, substituted alkoxy or an ester group; or
  $R_1$ and $R_2$, together with the carbon atoms to which they are attached, represent an oxirane ring; or
  $R_1$ and $R_2$, taken together, represent an akylidenedioxy or substituted alkylidenedioxy group; and
  $R_3$ represents —$CH_2R_6$,
    wherein
      $R_6$ represents an ester group, oxiranyl, or a group of formula

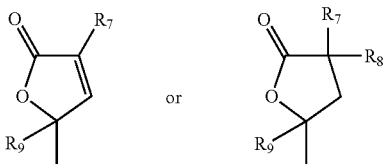

wherein
  $R_7$ represents hydrogen or alkyl,
  $R_8$ represents phenylsulfanyl, phenylselenyl, phenylsulfoxy or phenylselenoxy, and
  $R_9$ represents hydrogen, ethoxycarbonyl or carbamoyl; and
$R_4$ represents, independently, hydrogen, alkoxy or substituted alkoxy, or
$R_1$ and $R_4$, taken together, represent an alkylidenedioxy or a substituted alkylidenedioxy group;

In various embodiments, the compounds disclosed herein are used as arthropodicides.

In various further embodiments, the compounds disclosed herein are used as insecticides.

In various further embodiments, the compounds disclosed herein are used with special efficacy as insecticides with high toxicity in the control of fruit fly (*Drosophila melanogaster*), housefly (*Musca domestica*) and whitefly (*Trialeurodes vaporarium*).

In a third embodiment, the invention relates to the use, as pesticides, of a subgroup of compounds within the family of compounds of formula (I) or (I'), wherein
  $R_1$ and $R_2$ represent, independently from each other, hydrogen, alkoxy, substituted alkoxy or an ester group; or
  $R_1$ and $R_2$, together with the carbon atoms to which they are attached, represent an oxirane ring; or
  $R_1$ and $R_2$, taken together, represent an akylidenedioxy or substituted alkylidenedioxy group; and
  $R_3$ represents a group of formula

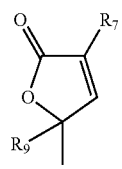

wherein
  $R_7$ represents hydrogen or alkyl, and
  $R_9$ represents hydrogen, ethoxycarbonyl or carbamoyl; and
$R_4$ represents, independently, hydrogen, alkoxy or substituted alkoxy, or
$R_1$ and $R_4$, taken together, represent an alkylidenedioxy or a substituted alkylidenedioxy group;

In a fourth embodiment, the invention relates to a subgroup of compounds within the family of compounds of formula (I), wherein
  ----- represents a carbon-carbon single bond;
  -----A----- represents —$CH(R_4)$—,
    wherein
      $R_4$ represents, independently, hydrogen, alkoxy or substituted alkoxy, or
      $R_1$ and $R_4$, taken together, represent an alkylidenedioxy or a substituted alkylidenedioxy group;
$R_1$ and $R_2$ represent, independently, hydrogen, alkoxy, substituted alkoxy or an ester group, or
$R_1$ and $R_2$, together with the carbon atoms to which they are attached, represent an oxirane ring; or
$R_1$ and $R_2$, taken together, represent an alkylidenedioxy or substituted alkylidenedioxy group; and
$R_3$ represents a group of formula

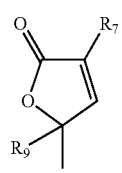

wherein
  $R_7$ represents hydrogen or alkyl, and
  $R_9$ represents hydrogen, ethoxycarbonyl or carbamoyl.

Preferred within this subgroup are the compounds of general formula (IA):

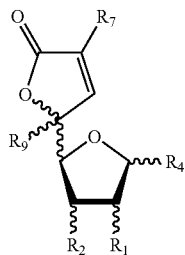

wherein $R_1$, $R_2$, $R_4$, $R_7$ and $R_9$ have the meanings indicated for this Fourth embodiment.

Especially preferred are the compounds of formula (IA), wherein $R_1$ and $R_4$, taken together, represent the isopropylidenedioxy group, $R_2$ represents benzyloxy, $R_7$ represents methyl and $R_9$ represents hydrogen.

Among these, the most especially preferred are the D-gluco derivative, i.e. 3-O-benzyl-6,7-dideoxy-1,2-O-isopropylidene-7-methyl-α-D-gluco-oct-6-enefuranurono-8,5-lactone or the D-alo derivative, i.e. 3-O-benzyl-6,7-dideoxy-1,2-O-isopropylidene-7-methyl-α-D-alo-oct-6-enefuranurono-8,5-lactone.

Also particularly preferred are compounds of formula (IA), wherein $R_1$ and $R_4$, taken together, represent the isopropylidenedioxy group, $R_2$ represents benzyloxy and $R_7$ and $R_9$ represent hydrogen.

Among these, the most especially preferred are the D-alo derivative, i.e. 3-O-benzyl-6,7-dideoxy-1,2-O-isopropylidene-α-D-alo-oct-6-enefuranurono-8,5-lactone and the D-gluco derivative, i.e. 3-O-benzyl-6,7-dideoxy-1,2-O-isopropylidene-α-D-gluco-oct-6-enefuranurono-8,5-lactone.

In a fifth embodiment, the invention relates to a subgroup of compounds within the family of compounds of formula (I), wherein ----- represents a carbon-carbon double bond;

-----A----- represents =C($R_5$)—C(=O)—, wherein, $R_5$ represents hydrogen or halogen;

$R_1$ represents hydrogen or halogen; and $R_3$ represents —CH$_2R_6$, wherein $R_6$ represents an ester group.

Preferred within this subgroup are the compounds of general formula (IB):

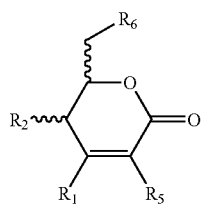

wherein $R_1$, $R_2$, $R_5$ and $R_6$ have the meanings indicated for this fifth embodiment.

Especially preferred are the compounds of formula (IB), wherein $R_1$ represents hydrogen, $R_2$ represents —OC(=O)CH$_3$, $R_5$ represents Br and $R_6$ represents —OC(=O)CH$_3$.

Among these, the most especially preferred is the D-erythro derivative, i.e. 4,6-di-O-acetyl-2-bromo-2,3-dideoxy-D-erythro-hex-2-ene-1,5-lactone.

In a sixth embodiment, the invention relates to a subgroup of compounds within the family of compounds of formula (I), wherein ----- represents a carbon-carbon single bond;

-----A----- represents —CH($R_4$)—, wherein $R_4$ represents, independently, hydrogen, alkoxy or substituted alkoxy, or $R_1$ and $R_4$, taken together, represent an alkylidenedioxy or substituted alkylidenedioxy group;

$R_1$ and $R_2$ represent, independently, hydrogen, alkoxy or substituted alkoxy, or $R_1$ and $R_2$, together with the carbon atoms to which they are attached, represent an oxirane ring; or $R_1$ and $R_2$, taken together, represent an alkylidenedioxy or a substituted alkylidenedioxy group; and $R_3$ represents a group of formula

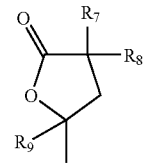

wherein $R_7$ represents hydrogen or alkyl, $R_8$ represents phenylsulfanyl, phenylselenyl, phenylsulfoxy or phenylselenoxy, and $R_9$ represents hydrogen, ethoxycarbonyl or carbamoyl.

Preferred within this subgroup are the compounds of general formula (IC):

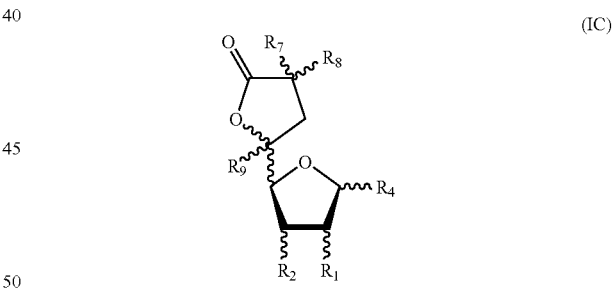

wherein $R_1$, $R_2$, $R_4$, $R_7$, $R_8$ and $R_9$ have the meanings indicated for this sixth embodiment.

Especially preferred are the compounds of formula (IC), wherein $R_1$ and $R_2$, together with the carbon atoms to which they are attached, form an oxirane ring, $R_4$ represents methoxy, $R_7$ represents methyl, $R_8$ represents phenylselenyl and $R_9$ represents hydrogen.

Among these, the most especially preferred is the 2,3-anhydro-β-L-gulo derivative, i.e. methyl (7R)- and methyl (7S)-2,3-anhydro-6,7-dideoxy-7-methyl-7-phenylselenyl-β-L-gulo-octofuranurono-8,5-lactone.

Also especially preferred are compounds of formula (IC), wherein $R_1$ and $R_4$, taken together, form an isopropylidenedioxy group, $R_2$ represents hydrogen, $R_7$ represents methyl, $R_8$ represents phenylselenyl and $R_9$ represents hydrogen.

Among these, the most especially preferred is the D-ribo derivative, i.e. (7R)- and (7S)-3,6,7-trideoxy-1,2-O-isopropylidene-7-methyl-7-phenylselenyl-α-D-ribo-octofuranuro-8,5-lactone.

Especially preferred are also the compounds of formula (IC), wherein $R_1$ and $R_4$, taken together, form an isopropylidenedioxy group, $R_2$ represents benzyloxy, $R_7$ represents methyl, $R_8$ represents phenylselenyl and $R_9$ represents hydrogen.

Among these, the most especially preferred is the D-gluco derivative, i.e. (7R)- and (7S)-3-O-benzyl-6,7-dideoxy-1,2-O-isopropylidene-7-methyl-7-phenylselenyl-α-D-gluco-octofuranurono-8,5-lactone.

In a seventh embodiment, the invention relates to a subgroup of compounds, within the family of compounds of formula (I), wherein ----- represents a carbon-carbon single bond;

-----A----- represents —CH($R_4$)—, wherein $R_4$ represents alkoxy or substituted alkoxy;

$R_1$ and $R_2$, taken together with the carbon atoms to which they are attached, represent an oxirane ring; and $R_3$ represents oxiranyl.

Preferred within this group are the compounds of general formula (ID):

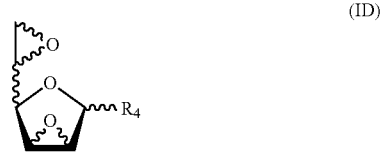

(ID)

wherein $R_4$ has the meaning indicated for this seventh embodiment.

Especially preferred are compounds of formula (ID), wherein $R_4$ represents methoxy.

Among these, the most preferred is the 2,3;5,6-dianhydro-β-L-gulo derivative, i.e. methyl 2,3;5,6-dianhydro-β-L-gulofuranoside.

In a eighth embodiment, the invention relates to a subgroup of compounds, within the family of compounds of formula (I), wherein ----- represents a carbon-carbon single bond;

-----A----- represents —CH($R_4$)—, wherein $R_4$ represents, independently, hydrogen, alkoxy or substituted alkoxy, or $R_1$ and $R_4$, taken together, represent an alkylidenedioxy or substituted alkylidenedioxy group; or $R_1$ and $R_2$ represent, independently, hydrogen, alkoxy or substituted alkoxy, or $R_1$ and $R_2$, taken together, represent an alkylidenedioxy or substituted alkylidenedioxy group; and $R_3$ represents oxiranyl.

Preferred within this subgroup are compounds of general formula (IE):

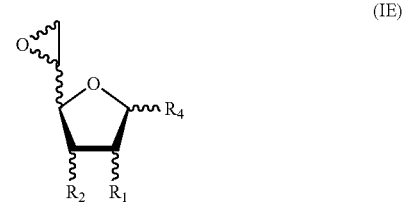

(IE)

wherein $R_1$, $R_2$ and $R_4$ have the meanings indicated for the eighth embodiment.

A second object of the present invention is a process for the preparation of compounds of formula (I).

Synthesis of Compounds of Formula (IA)

Compounds of formula (IA) can be prepared by oxidation of phenylsulfanyllactones with m-chloroperbenzoic acid or with sodium metaperiodate, leading to the formation of sulfoxides which, upon pyrolysis in toluene at reflux, provide the corresponding butenolides. The transformation of the phenylselenyllactones into butenolides results from the oxidation with hydrogen peroxide, under acid catalysis. This synthesis is summarized in the following Scheme 1.

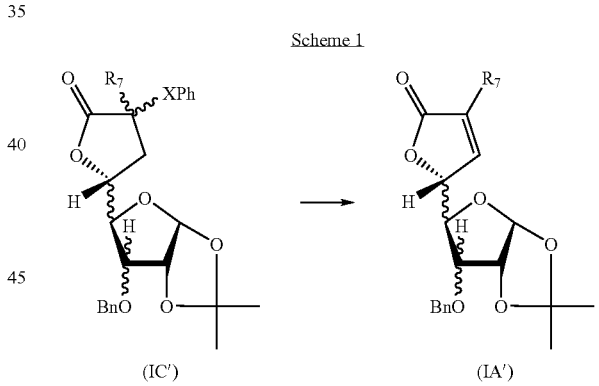

Scheme 1

In Scheme 1, a lactone of formula (IC') [compound of formula (IC), wherein $R_1$ and $R_4$ represent, taken together, isopropylidenedioxy, $R_2$ represents benzyloxy, $R_7$ represents hydrogen or methyl, $R_8$ represents XPh, wherein X represents S or Se, and $R_9$ represents hydrogen] is converted into a butenolide of formula (IA') [compound of formula (IA), wherein $R_1$ and $R_4$ represent, taken together, isopropylidenedioxy, $R_2$ represents benzyloxy, $R_7$ represents hydrogen or methyl and $R_9$ represents hydrogen]. This conversion is carried out in the presence of m-chloroperbenzoic acid (when X represents S) and toluene at reflux, or in the presence of hydrogen peroxide, in acid medium (when X represents Se), at temperatures between −20° C. and room temperature.

Synthesis of Compounds of Formula (IB)

Compounds of formula (IB) can be prepared according to Scheme 2.

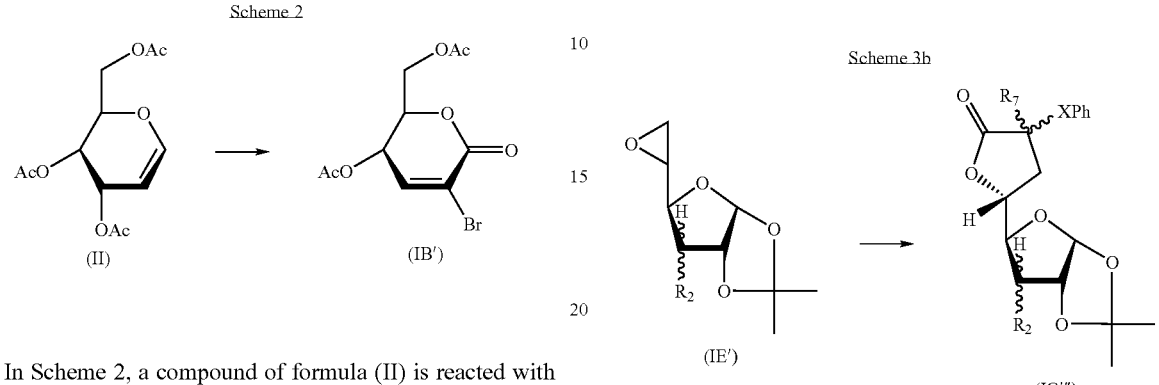

In Scheme 2, a compound of formula (II) is reacted with N-bromosuccinimide in the presence of tetrahydrofuran and water, at a temperature of 10° C. to 50° C., for a period of time from 4 to 24 hours. In a second step the product obtained is added to molecular sieves and pyridinium chlorochromate in dichloromethane, at a temperature of 10° C. to 50° C., for a period of time from 8 to 24 hours, to yield an α,β-unsaturated hexono-1,5-lactone of formula (IB') [compound of formula (IB), wherein $R_1$ represents hydrogen, $R_2$ and $R_6$ represent acetoxy and $R_5$ represents bromo].

Synthesis of Compounds of Formula (IC)

Compounds of formula (IC) can be prepared by reaction of the corresponding epoxide precursor with dianions, namely: dianion of phenylselenoacetic acid, phenylselenopropionic acid and phenylthioacetic acid, which upon cyclization in acid medium yield the corresponding phenylselenyllactones or phenylsulfanyllactones, according to Schemes 3a and 3b.

Scheme 3a

In Scheme 3a, a diepoxide of formula (ID') [compound of formula (ID), wherein $R_1$ and $R_2$ represent, taken together, oxiranyl and $R_4$ represents methoxy] is converted into a lactone of formula (IC") [compound of formula (IC), wherein $R_1$ and $R_2$ represent, taken together, oxiranyl, $R_4$ represents methoxy, $R_7$ represents hydrogen or methyl, $R_8$ represents XPh, wherein X represents S or Se, and $R_9$ represents hydrogen]. This conversion is carried out by treatment of (ID') with lithium diisopropropylamide in tetrahydrofuran, at a temperature between −10° C. and 10° C., followed by reaction with a compound of formula $PhXCHR_7CO_2H$ (wherein X represents S or Se e $R_7$ represents hydrogen or methyl).

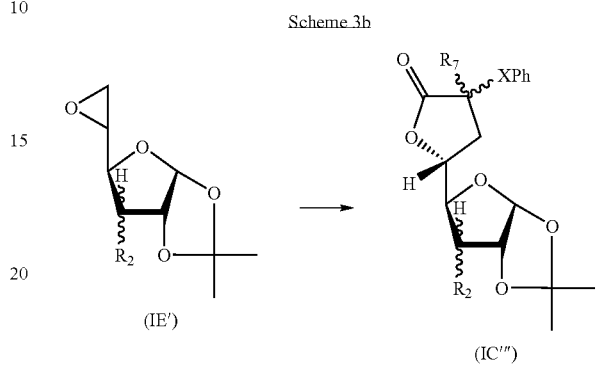

In Scheme 3b, following a procedure similar to that of Scheme 3a, an epoxide of formula (IE') [compound of formula (IE), wherein $R_1$ and $R_4$ represent, taken together, isopropylidenedioxy and $R_2$ represents benzyloxy or hydrogen] is converted into a lactone of formula (IC''') [compound of formula (IC), wherein $R_1$ and $R_4$ represent, taken together, isopropylidenedioxy, $R_2$ represents benzyloxy or hydrogen, $R_7$ represents hydrogen or methyl, $R_8$ represents XPh, wherein X represents S or Se, and $R_9$ represents hydrogen].

Synthesis of Compounds of Formula (ID)

Compounds of formula (ID) can be prepared according to Scheme 4.

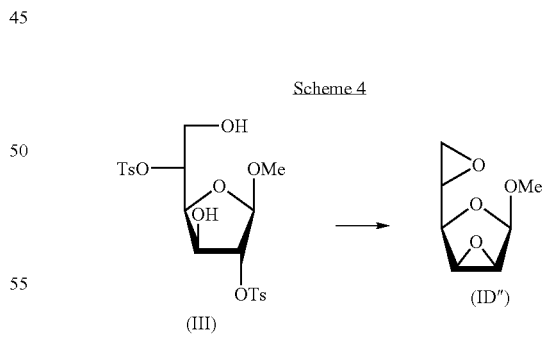

In Scheme 4, a compound of formula (III) is converted into a diepoxide of formula (ID") [compound of formula (ID), wherein $R_4$ represents methoxy]. This conversion is carried out by treatment of a compound of formula (III) with aqueous solution of potassium hydroxide and tetrahydrofuran, at a temperature between 5° C. and 40° C.

Synthesis of Compounds of Formula (IE)

Compounds of formula (IE) can be prepared according to Scheme 5.

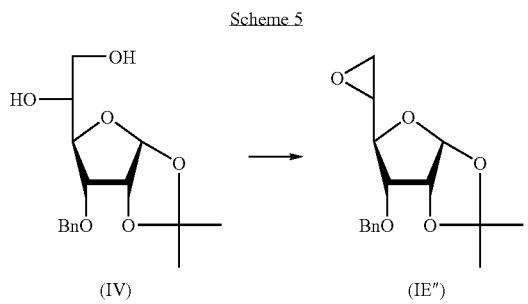

Scheme 5

(IV) → (IE″)

In Scheme 5, a compound of formula (IV) is converted into an epoxide of formula (IE″) [compound of formula (IE), wherein $R_1$ and $R_4$ represent, taken together, isopropylidenedioxy and $R_2$ represents benzyloxy]. This conversion is carried out by conversion of compound of formula (IV) with triphenylphosphane in benzene, followed by the addition of molecular sieves and diethyl azodicarboxylate, at a temperature between 60° C. and 100° C., for a period of time of 1 to 4 days.

A third object of the instant invention is the use of compounds of any of the above formulas as pesticides.

Preferably, these compounds are used as arthropodicides.

More preferably, these compounds are used as insecticides.

Still more preferably, these compounds are used with particular efficacy as insecticides of high toxicity for controlling fruit fly (*Drosophila melanogaster*), house fly (*Musca domestica*) and white fly (*Trialeurodes vaporarium*).

A fourth object of the invention is a method for controlling pests, namely arthropods, particularly insects, especially fruit fly, house fly and white fly. Said method comprises the application of an effective amount of compounds of formula (I) to said pests or their locus.

EXPERIMENTAL

PREPARATION EXAMPLES

Example 1

Preparation of 3-O-benzyl-6,7-dideoxy-1,2-O-isopropylidene-7-methyl-α-D-gluco-oct-6-enefuranurono-8,5-lactone (1)

Glacial acetic acid (1 drop) was added to a solution of (7R)- and (7S)-3-O-benzyl-6,7-dideoxy-1,2-O-isopropylidene-7-methyl-7-phenylselenyl-α-D-gluco-octofuranurono-8,5-lactone (130 mg, 0.26 mmol) in anhydrous tetrahydrofuran (0.26 mL) at 0° C. 30% $H_2O_2$ (6.70 eq.) was added dropwise and the reaction mixture was stirred for 45 min at 0° C. Extraction with a saturated solution of $NaHCO_3$ was followed by extraction with $CH_2Cl_2$ (3×2 mL). The organic phase was dried over sodium sulphate and evaporated under vacuum. The residue was purified by low pressure column chromatography to provide the title compound (45 mg, 64%) and unreacted starting material (26 mg, 20%); $R_f$: 0.40 (ethyl acetate/n-hexane 1:4); $[\alpha]_D^{20}$=−22 (c 1.0; $CHCl_3$); IR (neat): 1770 (C=O), 1378 z(C—O, isopropyl), 1662 (C=C) cm$^{-1}$; $^1$H NMR (300 MHz, $CDCl_3$): δ 7.35-7.30 (m, 6H, H-6, Ph), 5.93 (d, 1H, H-1, $J_{1,2}$=3.6 Hz), 5.17 (dd, 1H, H-5, $J_{4,5}$=8.6 Hz, $J_{5,6}$=1.5 Hz), 4.69 (s, 2H, $OCH_2Ph$), 4.63 (d, 1H, H-2), 4.14 (d, 1H, H-3, $J_{3,4}$=3.0 Hz), 3.91 (dd, 1H, H-4), 1.93 (s, 3H, Me-7), 1.48 (s, 3H, Me, isopropyl), 1.25 (s, 3H, Me, isopropyl); $^{13}$C NMR (75.43 MHz, $CDCl_3$): δ 174.0 (C=O), 148.7 (C-6), 137.1 (Cq, Ph), 130.2 (C-7), 128.5; 128.1; 127.8 (Ph), 112.3 (Cq, isopropyl), 105.3 (C-1), 82.3 (C-2), 81.8 (C-3), 81.5 (C-4), 76.8 (C-5), 72.8 ($OCH_2Ph$), 10.7 (Me-7), 26.73 (Me, isopropyl), 26.11 (Me, isopropyl). Anal. calcd for $C_{19}H_{22}O_6$ (346.35): C 65.89; H 6.39; Found: C 65.57; H 6.45%.

Example 2

Preparation of 3-O-benzyl-6,7-dideoxy-1,2-O-isopropylidene-7-methyl-α-D-alo-oct-6-enefuranurono-8,5-lactone (2)

Following a procedure similar to that of Example 1, starting from (7R)- and (7S)-3-O-benzyl-6,7-dideoxy-1,2-O-isopropylidene-7-methyl-7-phenylselenyl-α-D-gluco-octofuranurono -8,5-lactone[15] (100 mg, 0.2 mmol), the title compound was obtained (40 mg, 73% taking into account the starting material that reacted), with recovery of unreacted starting material (20 mg, 20%); $R_f$: 0.23 (ethyl acetate/n-hexane 1:3); $[\alpha]_D^{20}$=+122 (c 1.0; $CHCl_3$); IR (neat): 1786 (C=O), 1384 (C—O, isopropyl), 1662 (C=C) cm$^{-1}$; $^1$H NMR (300 MHz, $CDCl_3$): δ 7.41-7.30 (m, 5H, Ph), 7.25 (s, 1H, H-6), 5.77 (d, 1H, H-1, $J_{1,2}$=3.6 Hz), 5.16 (br s, 1H, H-5), 4.68; 4.64 (part A of AB system, $OCH_2Ph$, $J_{AB}$=12 Hz), 4.56 (t, 1H, H-2, $J_{2,3}$=4.4 Hz), 4.49; 4.45 (part B of AB system, 4.32 (dd, 1H, H-4, $J_{3,4}$=8.7 Hz, $J_{4,5}$=3.0 Hz), 3.65 (dd, 1H, H-3), 1.93 (s, 3H, Me-7), 1.55 (s, 3H, Me, isopropyl), 1.39 (s,3H, Me, isopropyl); $^{13}$C NMR (75.43 MHz, $CDCl_3$): δ173.8 (C=O), 145.3 (C-6), 136.9 (Cq, Ph), 130.4 (C-7), 128.5; 128.2; 128.0 (Ph), 113.3 (Cq, isopropyl), 104.1 (C-1), 79.3 (C-5), 78.6 (C-4), 72.1 ($OCH_2Ph$), 76.6 (C-2), 75.5 (C-3), 26.8 (Me, isopropyl), 26,5 (Me, isopropyl), 10.7 (Me-7). Anal. calcd for $C_{19}H_{22}O_6$ (346.35): C 65.89; H 6.39; Found: C 65.63; H 6.48%.

Example 3

Preparation of 3-O-benzyl-6,7-dideoxy-1,2-O-isopropylidene-α-D-alo-oct-6-enefuranurono-8,5-lactone (3)

Following a procedure similar to that of Example 1, starting from (7R)- and (7S)-3-O-benzyl-6,7-dideoxy-1,2-O-isopropylidene-7-phenylselenyl-α-D-alo-octofuranurono-8,5-lactone[15] (130 mg, 0.3 mmol) the title compound was obtained (100 mg, 91%). $R_f$ 0.60 (ethyl acetate/n-hexane 1:1); $[\alpha]_D^{20}$=+47 (c 0.5; $CH_2Cl_2$); IR (KBr): 1774 (C=O), 1382 (C—O, isopropyl), 1662 (C=C) cm$^{-1}$; $^1$H NMR (300 MHz, $CDCl_3$): δ 7.42 (d, H-6, $J_{6,7}$=6 Hz), 7.36-7.29 (m, 5H, Ph), 6.08 (dd, H-7, $J_{5,7}$=2.1 Hz), 5.7 (d, H-1, $J_{1,2}$=3.6 Hz), 5.28 (br s, H-5), 4.65; 4.61, 4.47 and 4.43 (AB system, $OCH_2Ph$, $J_{AB}$=12 Hz), 4.51 (dd, H-2, $J_{2,3}$=4.2 Hz), 4.33 (dd, H-4, $J_{4,5}$=3.3 Hz, $J_{3,4}$=9 Hz), 3.62 (dd, H-3), 1.59 (s, 3H, Me, isopropyl), 1.35 (s, 3H, Me, isopropyl); $^{13}$C NMR (75.43 MHz, $CDCl_3$): δ 173.8 (C=O), 152.9 (C-6), 136.4 (Cq, Ph), 128.6; 128.3 (Ph), 121.9 (C-7), 112.0 (Cq, isopropyl), 104.3 (C-1), 86.8 (C-5), 81.5 (C-4), 78.5 (C-2), 72.2 ($OCH_2Ph$), 68.0 (C-3), 26.5 (Me, isopropyl), 26.3 (Me, isopropyl). Anal. calcd for $C_{18}H_{20}O_6$ (332.33): C 65.06; H 6.06; Found: C 65.05; H 6.29%.

Example 4

Preparation of 3-O-benzyl-6,7-dideoxy-1,2-O-isopropylidene-α-D-gluco-oct-6-enefuranurono-8,5-lactone (4)

Following a procedure similar to that of Example 1, starting from (7R)- and (7S)-3-O-benzyl-6,7-dideoxy-1,2-O-isopropylidene-7-phenylselenyl-α-D-gluco-octofuranurono-8,5-lactone[13,15] (112 mg, 0.23 mmol) the title compound was obtained (57.4 mg, 75%). $R_f$ 0.32 (ethyl acetate/n-hexane 1:4); m.p.=66-70° C.; $[α]_D^{20}$=+0.2 (c 0.5; $CHCl_3$); IR ($CHCl_3$): 1758 (C=O), 1380 (C—O, isopropyl) $cm^{-1}$; $^1H$ NMR (300 MHz, $CDCl_3$): δ 7.71 (dd, H-6, $J_{6,7}$=5.9 Hz), 7.37-7.31 (m, 5H, Ph), 6.15 (dd, H-7, $J_{5,7}$=1.5 Hz), 5.92 (d, H-1, $J_{1,2}$=3.5 Hz), 5.30 (dd, H-5, $J_{5,6}$=1.5 Hz), 4.73-4.65 (AB system, $OCH_2Ph$, $J_{AB}$=11 Hz), 4.63 (d, 1H, H-2), 4.15 (d, H-3, $J_{3,4}$=3.5 Hz), 3.97 (dd, H-4, $J_{4,5}$=6.7 Hz), 1.29 (s, 3H, Me, isopropyl), 1.43 (s, 3H, Me, isopropyl); $^{13}C$ NMR (75.43 MHz, $CDCl_3$): δ 172.7 (C=O), 156.5 (C-6), 137.0 (Cq, Ph), 128.6; 128.3; 128.1 (Ph), 121.7 (C-7), 112.3 (Cq, isopropyl), 105.4 (C-1), 82.3 (C-2), 81.8 (C-3), 81.2 (C-4), 79.2 (C-5), 72.9 ($OCH_2Ph$), 26.8 (Me, isopropyl), 26.2 (Me, isopropyl). Anal. calcd for $C_{18}H_{20}O_6$ (332.33): C 65.06; H 6.06; Found: C 64.79; H 6.20%.

Example 5

Preparation of compound 4,6-di-O-acetyl-2-bromo-2,3-dideoxy-D-erythro-hex-2-enone-1,5-lactone (5)

N-bromosuccinimide (780 mg, 4.88 mmol) was added to a solution of tri-O-acetyl-D-glucal (1 g, 3.67 mmol) in 370 mL tetrahydrofuran (THF) and 92 mL distilled water. The mixture was stirred overnight at room temperature. The reaction mixture was poured into water chilled at 0° C., followed by extraction of the mixture thus obtained with diethyl ether. The combined organic phases were dried over sodium sulphate, filtered and the solvent was removed at reduced pressure to afford a syrup. The residue was then added to a suspension of 3 Å molecular sieves (6.8 g) and pyridinium chlorochromate (4.4 g) in dichloromethane (20 mL). The reaction mixture was stirred at room temperature overnight, eluted with diethyl ether and stirred at room temperature for 10 min. The precipitate was removed by filtration and the filtrate was poured over florisil in a filter and filtered under vacuum. The colourless filtrate was concentrated under reduced pressure to provide the title compound as a syrup (760 mg, 37%). $[α]_D^{20}$=+121 (c 1, $CH_2Cl_2$); IR (neat): 1752 $cm^-$(C=O, lactone); 1632 $cm^{-1}$ (C=C); $^1H$ NMR (300 MHz, $CDCl_3$): δ 7.01 (d, 1H, H-3, $J_{3,4}$=3.9 Hz); 5.30 (dd, 1H, H-4, $J_{4,5}$=6.6 Hz); 4.19, 4.17, 4.15, 4.13 (H-6a, part A of AB system, $J_{6a,6b}$=12.6, $J_{5,6a}$=4.5 Hz); 4.10, 4.08, 4.06, 4.04 (H-6b, part B of AB system, $J_{5,6b}$=3.6 Hz); 1.91 (s, 3H, acetyl $CH_3$); 1.85 (s, 3H, acetyl $CH_3$); $^{13}C$ NMR (75.43 MHz, $CDCl_3$): δ170.1, 169.0 (acetyl C=O); 157.1 (lactone C=O); 142.3 (C-3); 116.4 (C-2); 77.7 (C-4); 64.8 (C-5); 61.6 (C-6); 20.4 (acetyl $CH_3$); Anal. calcd for $C_{10}H_{11}O_6Br$ (307.08): C 39.12; H 3.61; Found: C 39.13; H 3.62%.

Example 6

Preparation of methyl (7R)-/(7S)-2,3-anhydro-6,7-dideoxy-7-methyl-7-phenylselenyl-β-L-gulo-octofuranurono-8,5-lactone (6A/6B)

A solution of n-BuLi (1.6 M in n-hexane, 5.43 mL, 8.7 mmol) was added dropwise to a solution of diisopropylamine (1.22 mL, 8.7 mmol) in anhydrous tetrahydrofuran (16 mL) under argon atmosphere at 0° C., and the mixture was stirred at 0° C. for 25 min. A solution of phenylselenoacetic, phenylselenopropionic or phenylthioacetic acid (3.9 mmol) in anhydrous tetrahydrofuran (4 mL) was added dropwise to the reaction mixture, keeping the temperature at 0° C. and the mixture was stirred for 1 h at 0° C. A solution of methyl 2,3;5,6-dianhydro-β-L-gulofuranoside (compound of Example 9, 624 mg, 3.95 mmol) in anhydrous tetrahydrofuran (3 mL/g of compound of Example 9) was then added dropwise and the reaction mixture was stirred first at 0° C. for 1 h and then at room temperature for 16 h. After addition of a solution of 50% acetic acid (10 mL) and heating under reflux for six hours, the mixture was cooled to room temperature and neutralized with a saturated solution of $NaHCO_3$. After extraction of the mixture with diethyl ether (3×20 mL), the combined organic phases were washed with water and dried over sodium sulphate. Evaporation of the solvent under vacuum and purification by low pressure column chromatography, gave the title compounds (460 mg, 32%, 6A/6B: 3/1). $R_f$=0.23 (ethyl acetate/n-hexane 1:1); IR (neat): 1784 (C=O), 1286 (C—O, epoxide) $cm^{-1}$; $^1H$ NMR (300 MHz, $CDCl_3$) of 6A: δ 7.68-7.65 (m, 2H, Ph), 7.48-7.36 (m, 3H, Ph), 5.08 (s, 1H, H-1), 4.77 (ddd, 1H, H-5, $J_{4,5}$=6.9 Hz, $J_{5,6a}$=5.7 Hz, $J_{5,6b}$=10.5 Hz), 4.02 (d, 1H, H-4, $J_{34}$=6.6 Hz), 3.74 (d, 1H, H-3, $J_{2,3}$=2.7 Hz), 3.68 (d, 1H, H-2), 3.55 (s, 3H, $OCH_3$), 2.52 (dd, 1H, H-6a, $J_{6a,6b}$=14.1 Hz), 2.32 (dd, 1H, H-6b), 1.66 (s, 3H, Me); $^{13}C$ NMR (75.43 MHz, $CDCl_3$) of 6B: δ 176.0 (C-8), 137.7 (Cq, Ph), 129.7; 128.9 (Ph), 102.2 (C-1), 77.0 (C-4), 75.7 (C-5), 56.8 (OMe), 54.7 (C-2), 53.4 (C-3), 44.5 (C-7), 39.0 (C-6), 23.9 (Me). Anal. calcd for $C_{16}H_{18}O_5Se$ (369.25): C 52.04; H 4.90; Found: C 51.78; H 4.95%.

Example 7

Preparation of (7R)-/(7S)-3,6,7-Trideoxy-1,2-O-isopropylidene-7-methyl-7-phenylselenyl-α-D-ribo-octofuranurono-8,5-lactone (7A/7B)

Following a procedure similar to that of Example 6, starting from 5,6-anhydro-3-deoxy-1,2-O-isopropylidene-α-D-ribo-hexofuranose[15] (380 mg, 2.04 mmol), the title compounds were obtained (470 mg, 58%, 7A/7B: 7/3), after separation by column chromatography with ethyl acetate/n-hexane (1:3) as eluent; $R_f$=0.27 (ethyl acetate/n-hexane (1:3); IR (KBr): 1754 (C=O), 1378 (C—O, isopropyl) $cm^{-1}$; $^1H$ NMR (300 MHz, $CDCl_3$) of 7A: δ 7.74-7.67 (m, 2H, Ph), 7.49-7.29 (m, 3H, Ph), 5.84 (d, 1H, H-1, $J_{1,2}$=3.3 Hz), 4.78 (t, 1H, H-2, $J_{2,3b}$=3.9 Hz), 4.48-4.41 (ddd, 1H, H-5, $J_{4,5}$=5.1 Hz, $J_{5,6b}$=10.1 Hz), 4.31-4.24 (ddd, 1H, H-4), 2.52 (dd, 1H, H-6a, $J_{5,6a}$=5.5 Hz, $J_{6a,6b}$=14.1 Hz), 2.27-2.14 (m, 2H, H-6b, H-3a), 1.73-1.66 (m, 4H, H-3b, Me), 1.53 (s, 3H, Me), 1.35 (s, 3H, Me). $^{13}C$ NMR (75.43 MHz, $CDCl_3$) of 7B: δ 176.4 (C=O), 137.8 (Cq, Ph), 129.9; 129.1 (Ph), 111.6 (Cq, isopropyl), 105.6 (C-1), 80.2 (C-2), 78.6 (C-4), 76.9 (C-5), 44.7 (C-7), 40.5 (C-6), 35.1 (C-3), 26.7 (Me), 26.1 (Me), 24.0 (Me). Anal. calcd for $C_{18}H_{22}O_5Se$ (397.30): C 54.41; H 5.57; Found: C 54.79; H 5.72%.

Example 8

Preparation of (7R)-/(7S)-3-O-Benzyl-6,7-dideoxy-1,2-O-isopropylidene-7-methyl-7-phenylselenyl-α-D-gluco-octofuranurono-8,5-lactone (8A/8B)

Following a procedure similar to that of Example 6, starting from 5,6-anhydro-3-O-benzyl-1,2-O-isopropylidene-α-

D-glucofuranose (430 mg, 1.47 mmol), the title compounds were obtained (590 mg, 79%, 8A/8B: 1/2), after separation by chromatography with ethyl acetate/n-hexane (1:6) as eluent; $R_f$=0.49 (ethyl acetate/n-hexane 1:6); IR (neat): 1773 (C=O), 1382 (C—O, isopropyl) cm$^{-1}$; $^1$H NMR (300 MHz, CDCl$_3$): δ 7.67-7.63 (m, 4H, Ph), 7.41-7.26 (m, 16H, Ph), 5.95 (d, 1H, H-1A, $J_{1,2}$=3.6 Hz), 5.90 (d, 1H, H-1B, $J_{1,2}$=3.6 Hz), 4.83-4.17 (m, 7H, OCH$_2$Ph, H-2, H-5A) 4.18 (dd, 1H, H-4A, $J_{3,4}$=10.2 Hz, $J_{4,5}$=3.3 Hz), 4.09-4.05 (m, 2H, H-3), 3.78-3.75 (dd, 1H, H-4B, $J_{3,4}$=7.2 Hz, $J_{4,5}$=3.3 Hz), 3.16 (d, 1H, H-5B, $J_{5,6}$=3.9 Hz), 2.94 (dd, 1H, H-6aB, $J_{5,6a}$=3.9 Hz, $J_{6a,6b}$=5.1 Hz), 2.79 (dd, 1H, H-6bB, $J_{5,6b}$=2.4 Hz), 2.59 (dd, 1H, H-6aA, $J_{5,6a}$=5.7 Hz $J_{6a,6b}$=14.4 Hz), 2.38 (dd, 1H, H-6bA, $J_{5,6b}$=9.9 Hz), 1.63 (s, 6H, Me-7), 1.51 (s, 6H, Me, isopropyl), 1,31 (s, 6H, Me, isopropyl); $^{13}$C NMR (75.43 MHz, CDCl$_3$): δ 176.7 (C=O), 137.6 (CqPh), 129.8; 129.0; 128.5; 128.1; 127.8; 127.6 (Ph), 112.1 (Cq-isopropyl), 105.2 (C-1), 82.6 (C-2), 82.5, 82.0 (C-3), 81.7, 81.5 (C-4), 73.1 (C-5A), 72.6 (OCH$_2$Ph), 48.2 (C-5B), 46.9 (CH$_2$-6A), 45.0, 44.2 (C-7), 41.3 (CH$_2$-6B), 26.8 (Me, isopropyl), 26.2 (Me, isopropyl), 24.0 (Me-7). Anal. calcd for C$_{25}$H$_{28}$O$_6$Se (503.42): C 59.65; H 5.60; Found: C 60.00; H 5.93%.

Example 9

Methyl 2,3;5,6-Dianhydro-β-L-gulofuranoside (9)

a) Preparation of methyl 2,5-di-O-tosyl-β-D-glucofuranoside

A solution of 1-O-methyl-2,5-O-ditosyl-β-D-glucofuranurono-6,3-lactone[29] (500 mg, 1 mmol) in tetrahydrofuran (10 mL) was added dropwise over 1 h to a suspension of LiBH$_4$ (42 mg, 1.93 mmol) in tetrahydrofuran (5 mL), previously cooled to −10° C. The reaction mixture was then stirred at +14° C. for 16 h. After neutralisation with acetic acid (50% in H$_2$O), filtration and concentration under reduced pressure a syrup was obtained which was treated with MeOH (3×5 mL) and concentrated under vacuum. The residue was dissolved in ethyl acetate and extracted with water. The organic phase was dried over sodium sulphate and evaporated at reduced pressure. The residue was purified by column chromatography with ethyl acetate/toluene (1:3) as eluent to give the title compound (472 mg, 94%). $R_f$: 0.25 (ethyl acetate/toluene 1:3); $[α]_D^{20}$=+44 (c 1, CHCl$_3$); IR (KBr): 3500 (OH) cm$^{-}$; $^1$H NMR (300 MHz, CDCl$_3$): δ 7.85-7.82 (m, 4H, Ph), 7.41-7.37 (m, 4H, Ph), 4.92-4.88 (m, 2H, H-1, H-5), 4.70 (s, 1H, H-2), 4.35 (t, 1H, H-3, $J_{3,OH}$=8.1 Hz), 4.32 (dd, 1H, H-4, $J_{4,5}$=3.9 Hz, $J_{3,4}$=8.4 Hz), 3.90-3.82 (m, 2H, H-6a, H-6b), 3.31 (s, 3H, OCH$_3$), 2.46 (s, 3H, CH$_3$Ph), 2.45 (s, 3H, CH$_3$Ph); $^{13}$C NMR (75.43 MHz, CDCl$_3$): δ 145.0; 145.1 (Cq, Ph), 130.0; 129.8; 128.8; 127.9 (CH, Ph), 100.8 (C-1), 83.3 (C-2), 79.2 (C-5), 76.7 (C-4), 73.5 (C-3), 61.7 (C-6), 56.0 (OMe), 21.7 (CH$_3$, Ts). Anal. calcd for C$_{21}$H$_{26}$O$_{10}$S$_2$ (502.54): C 50.21; H 5.21; S 12.76; Found: C 50.23; H 5.30; S 12.65%.

b) Methyl 2,3;5,6-dianhydro-β-L-gulofuranoside

A solution of KOH (56 mg, 1.0 mmol) in water (1 mL) was cooled to +10° C. and added to a solution of methyl 2,5-di-O-tosyl-β-D-glucofuranoside (compound of step a)) (202 mg, 0.4 mmol) in water (4.0 mL) and tetrahydrofuran (1.0 mL), previously cooled to +10° C. The reaction mixture was stirred at room temperature, until monitoring by thin layer chromatography showed that the reaction was completed. After extraction with CHCl$_3$ (10×10 mL), the combined organic phases were dried over sodium sulphate and concentrated at reduced pressure. The residue was purified by column chromatography with ethyl acetate/toluene (1:3) to provide the title compound (61 mg, 97%); $R_f$: 0.5 (ethyl acetate/n-hexane 1/1); $[α]_D^{20}$=+66 (c 0.5; CH$_2$Cl$_2$); $^1$H NMR (300 MHz, CDCl$_3$): δ 5.01 (s, 1H, H-1), 3.78 (d, 1H, H-4, $J_{4,5}$=6.0), 3.68-3.65 (m, 2H, H-2, H-3), 3.43 (s, 3H, OCH$_3$), 3.19 (ddd, 1H, H-5), 2.87 (dd, 1H, H-6a, $J_{5,6a}$=4.2 Hz ), 2.75 (dd, 1H, H-6b, $J_{5,6b}$=3 Hz, $J_{6a,6b}$=6 Hz); $^{13}$C NMR (75.43 MHz, CDCl$_3$): δ 102.4 (C-1), 76.7 (C-4), 55.7 (OMe), 55.6 (C-2), 53.7 (C-3), 50.4 (C-5), 44.0 (C-6). Anal. calcd for C$_7$H$_{10}$O$_4$ (158.14): C 53.16; H 6.36; Found: C 53.13; H 6.35%.

Example 10

Preparation of 5,6-anhydro-3-O-benzyl-1,2-O-isopropylidene-α-D-alofuranose

Triphenylphosphane (2.6 eq.) was added to a solution of 3-O-benzyl-1,2-O-isopropylidene-α-D-alofuranose[28] (2.40 g, 8.2 mmol) in benzene (143.5 mL) and the mixture was stirred at room temperature for 15 min. After addition of powdered 3 Å molecular sieves (6.56 g), diethyl azodicarboxylate (2.6 eq.) was added dropwise and the reaction mixture was stirred at 80° C. for 48 h. After filtration and evaporation of the solvent, the residue was purified by low pressure column chromatography to provide the title compound (1.75 g, 73%) as a syrup after purification by column chromatography with the system ethyl acetate/n-hexane (1:3); $R_f$=0.41 (ethyl acetate/n-hexane 1:3); $[α]_D^{20}$=+62 (c 1.0; CHCl$_3$); IR (neat): 1262 (C—O, epoxide), 1380 (C—O, isopropyl) cm$^{-1}$; $^1$H NMR (300 MHz, CDCl$_3$): δ 7.39-7.29 (m, 5H, Ph), 5.74 (d, 1H, H-1, $J_{1,2}$=3.6 Hz), 4.76; 4.72 (part A of AB system, OCH$_2$Ph, $J_{A,B}$=11.7 Hz), 4.59-4.55 (m, 2H, H-2, OCH$_2$Ph, part B of AB system), 3.66 (dd, 1H, H-3, $J_{2,3}$=4.2 Hz, $J_{3,4}$=8.7 Hz), 3.19-3.16 (m, 1H, H-5), 4.20 (dd, 1H, H-4, $J_{4,5}$=3.0 Hz), 2.79-2.73 (m, 2H, H-6a, H-6b), 1.53 (s, 3H, Me), 1.37 (s, 3H, Me); $^{13}$C NMR (75.43 MHz, CDCl$_3$): δ 137.1 (Cq, Ph), 128.5; 128.3; 127.9 (Ph), 112.8 (Cq, isopropyl), 103.8 (C-1), 71.8 (OCH$_2$Ph), 77.5 (C-2), 77.0 (C-3), 76.5 (C-4), 50.4 (C-5), 44.2 (C-6), 26.6 (Me), 26.4 (Me). Anal. calcd for C$_{16}$H$_{20}$O$_5$ (292.3): C 65.74; H 6.88; Found: C 65.40; H 6.88%.

Biological Activity of the Compounds

Materials and Methods for Determination of Biological Activity

A range of arthropod species was chosen to represent those in the terrestrial, aerial and aquatic environment, covering important target pest groups such as house and fruit flies and the white fly, which belongs to a group of agricultural and horticultural pests.

Method A

Topical Treatment of Adult Fruit Fly (*D. melanogaster*)

A culture of fruit flies (*D. melanogaster*) was used in the production of adult flies (approx 0.22 mg) of about seven days.

Serial dilutions of the compounds were prepared in acetone, and volumes of approximately 0.2 μL were applied to the ventral surface of each insect, using a calibrated PAX 100 microapplicator and a 1 mL syringe.

The fruit flies, in groups of 5, were anaesthetised using carbon dioxide. Prior to recovery the flies were placed in a containing vial and kept at 30±1° C., for observations of mortality at 1, 2, 3 and 24 hours after treatment.

For this purpose solutions of 6 different concentrations and a control were employed in groups of 12 and 20 insects. Control mortalities were normally zero but occasionally rose to 5-10%.

Method B

Second Method for Topical Treatment of Adult Fruit Flies

Different dilutions of the compounds in acetone were prepared and applied to individual fruit flies using a Gilson piston micropipette.

Individual flies were held in padded forceps and 1 μL of acetone solution was applied. The acetone was allowed to evaporate before placing the fly into the vial for observation, kept at 30±1° C., following the standard methodology.

Method C

Method by Feeding Adult Fruit Fly (*D. melanogaster*)

Large glass vials were used which were fitted with caps, inside of which is inserted a piece of cotton wool. This was soaked in a 10% sugar solution containing the test compounds in a given concentration.

Care was taken to ensure that no solution dripped from the cotton wool and condensation was avoided by keeping the vials at room temperature (25° C.).

The fruit flies were anaesthetised using carbon dioxide and placed in the vials for recovery and feeding.

Method D

Topical Treatment of Fruit Fly Larvae

Fruit fly larvae were separated from the growing medium and second and third instars were topically treated with 0.2 μL acetone solutions of the compounds using a PAX microapplicator.

Larvae were held in padded forceps for dosing and then placed on moistened filter paper, at 30±1° C., for observation.

Method E

Topical Treatment of House Fly Adults (*M. domestica*)

A culture of an insecticide-susceptible strain, Cooper, was established. Three-day-old adult house flies (body weight about 1.8 mg) were anaesthetised with carbon dioxide. Using the PAX microapplicator, a volume of 1 μL of acetone solution of the test compounds was applied to the dorsal cuticle, holding the fly in padded forceps.

Groups of flies were placed into closed vials, kept at 30±1° C., for observation.

Method F

Immersion Bioassay of Brine Shrimp *A. salina* Larvae in Brine

Freshly hatched brine shrimps were prepared by adding aquarium brine shrimp eggs to salt water (15 g sea salt per liter water). The following day hatchlings were separated from eggs and empty egg cases, using their phototropic movement and a Pasteur pipette.

Into each of a set of small glass vials was pipetted 195 μL of brine containing 5 shrimp larvae, using a micropipette. The solution of the test compound in 5 μL acetone was added, the vial closed and kept at 30±1° C. for observation.

Dead and alive shrimps were counted, at 1 and 24 hours after treatment, using a microscope. Six concentrations and a control were used with 10 shrimps treated.

A blank test was performed for comparison of the results.

Method G

Foliar Treatment of Glasshouse White Fly (*T. vaporariorum*)

Seedlings of tomato plants were infested with adult white fly. Selected leaves of the tomato plants were excised and carefully trimmed to 3 leaflets without disturbing the infestation. These were placed in glass tubes containing water and the leaflets were then sprayed on both sides with a small sprayer delivering for each one 200 μL of a solution of the test compound dissolved in 30% acetone in water.

Controls were sprayed with the solvent alone.

Counts of insects on the individual leaflets were made immediately after spraying and then at 14 hours following.

Calculation of Toxicity Parameters

Dosages used in insect treatments were based upon the amount of compound applied to each insect. For the shrimps the final concentrations of the compounds in the immersion brine were used.

The 24 hour mortalities were used to calculate the $LD_{50}/LC_{50}$ using regression analysis of the probability percent mortality (probit) against log dose/concentration.[30] This was calculated using PoloPC software (LeOra Software, Berkeley, Calif., 1994).

Where single dose treatments were used (in the case of whitefly assays), no statistics are available and the results are expressed as percent effect.

Results

Toxicity to Fruit Fly (*D. Melanogaster*)

The results of assays with fruit fly *D. Melanogaster* are given in Table 1.

In the table are also given the confidence intervals at 95% for the $LD_{50}$ values, the number of organisms tested, the slope obtained by linear regression and the index g (of significance). Data are considered satisfactory if g is substancially less than 1 and seldom greater than 0.4.[31]

As regards the confidence intervals for $LD_{50}$, the indication (90%) means that the intervals were calculated at 90% and not at 95%.

From the analysis of the $LD_{50}$ values, calculated through method 1, it is found that in general the compounds tested are active against adult fruit flies, compounds of Examples 1, 2, 3 and 9 being extremely active.

All of them are more active than imidacloprid, the reference insecticide for fruit fly.

TABLE 1

Toxicity parameters of compounds tested on fruit flies according to methods A, B and D.

| Compound No. | $LD_{50}$ (μg/insect) | Confidence Intervals at 95% for $LD_{50}$ (μg/insect) | No. of Organisms Tested | Slope | g |
|---|---|---|---|---|---|
| Method A | | | | | |
| 1 | 0.00002 | 0.00000-0.00011 | 124 | 0.500 ± 0.124 | 0.238 |
| 2 | 2.27 × 10$^{-6}$ | 0.00000-0.00002 | 150 | 0.308 ± 0.066 | 0.175 |
| 3 | 5.02 × 10$^{-6}$ | 0.00000-0.00008 | 114 | 0.340 ± 0.104 | 0.362 |
| 4 | 0.00012 | n.d. | 114 | 0.385 ± 0.109 | 0.860 |
| 5 | 0.00016 | 0.00000-0.00226 | 114 | 0.296 ± 0.096 | 0.401 |
| 6 | 0.00015 | 0.00000-0.00092 | 114 | 0.696 ± 0.155 | 0.484 |
| 7 | 0.00020 | 0.00000-0.00154 (90%) | 114 | 0.395 ± 0.104 | 0.527 |
| 8 | 0.00037 | n.d. | | 0.453 ± 0.115 | 0.967 |
| 9 | 0.00003 | 0.00000-0.00043 | 114 | 0.326 ± 0.106 | 0.405 |
| Imidacloprid | 0.01253 | 0.00523-0.01637 | 75 | 2.218 ± 0.911 | 0.648 |
| Method B | | | | | |
| 2 | 0.00398 | 0.00000-0.2415 (90%) | 48 | 0.484 ± 0.206 | 0.693 |
| Method D | | | | | |
| 5 | 4.74974 | 3.21963-20.59868 (90%) | 75 | 1.602 ± 0.674 | 0.681 |
| 7 | 0.96796 | 0.72391-2.06494 | 75 | 2.624 ± 0.810 | 0.366 | n.d.—Data not available

The fruit fly larvae are less sensitive to the toxins than adult flies.

The values of $LD_{50}$ obtained for the compounds of Examples 5 and 8 are much higher than those obtained for the adult fly, therefore these compounds are less toxic for larvae than for adult flies.

Toxicity to House Fly *M. domestica*

Toxicity parameters for adult house flies, treated topically with compounds of Examples 5 and 8, are given in Table 2.

Although these insects are approximately 8 fold larger than fruit flies, analysis of said table allows to conclude that the compounds tested are much less toxic (2 to 3 orders of magnitude) for this type of flies than for fruit flies.

$LD_{50}$ values correspond only to a moderate insecticidal activity.

TABLE 2

Toxicity parameters of compounds tested on adult house flies

| Compound No. | $LD_{50}$ (μg/insect) | Confidence Intervals at 95% for $LD_{50}$ (μg/insect) | No. of Organisms Tested | Slope | g |
|---|---|---|---|---|---|
| Method E | | | | | |
| 5 | 1.06481 | n.d. | 40 | 0.228 ± 0.146 | 1.561 |
| 8 | 0.64404 | n.d. | 30 | 0.383 ± 0.182 | 0.863 |

Toxicity to Brine Shrimp

Toxicity parameters for assays in which brine shrimp larvae are exposed to the compounds in saline solution are given in Table 3. Data obtained show good correlation (g<0.4) and high $LC_{50}$ values, indicating a low toxicity for this type of organisms.

TABLE 3

Toxicity parameters of compounds tested on brine shrimp larvae, method F.

| Compound No. | $LC_{50}$ (μg/mL) | Confidence Intervals at 95% for $LC_{50}$ (μg/mL) | No. of Organisms Tested | Slope | g |
|---|---|---|---|---|---|
| Method F | | | | | |
| 1 | 100.62 | 90.03-125.27 | 50 | 8.862 ± 2.644 | 0.342 |
| 2 | 64.30 | 57.75-77.28 | 50 | 9.217 ± 2.638 | 0.315 |
| 3 | 144.71 | 128.12-172.71 | 50 | 7.763 ± 2.182 | 0.303 |
| 4 | 358.92 | 324.89-400.42 | 60 | 9.770 ± 2.057 | 0.170 |
| 5 | 38.36 | 8.244-3258.70 (90%) | 60 | 0.423 ± 0.175 | 0.655 |
| 6 | 125.48 | 113.08-139.97 | 50 | 10.275 ± 2.421 | 0.213 |
| 7 | 261.04 | 220.59-320.09 (90%) | 50 | 8.601 ± 2.195 | 0.778 |
| 8 | 220.41 | 199.24-249.71 | 50 | 10.359 ± 2.659 | 0.253 |
| 9 | 671.50 | 567.31-807.72 (90%) | 60 | 8.734 ± 1.862 | 0.591 |
| Imidacloprid | 0.03121 | 0.02387-0.04593 | 100 | 2.435 ± 0.802 | 0.417 |

Insecticidal Effect on Adult White Fly

The results of the bioassays of the insecticidal compounds on adult whiteflies *T. vaporariorum* are given in Table 4. Five compounds were tested, which were applied spraying 600 µL of each compound solution (prepared according to method G) on the leaves of tomato plants infested with a known number of adult whitefly. After 14 hours, the number of dead insects (or eventually of insects that disappeared) was counted. These assays were performed at room temperature, between 20 and 25° C.

From the data in Table 4, it is found that the compounds of Examples 4 and 9 show effiacy as insecticides.

TABLE 4

Insecticidal effect againts adult white fly, assayed by spraying infested tomato leaves.

| Compound No. | Concentration (µg/mL) | % Control of White Fly |
|---|---|---|
| 3 | 1.3 | 0 |
| 4 | 2.5 | 50 |
| 6 | 1.3 | 0 |
| 7 | 4.8 | 0 |
| 9 | 2.5 | 85 |

DISCUSSION AND CONCLUSIONS

Bioassays were performed using a range of compounds and treatment techniques in different species of arthropods. Adult fruit flies, treated topically, showed high levels of sensitivity to the compounds tested, such that the $LD_{50}$ values determined are much lower than that for the reference insecticide "imidacloprid". However some variation was observed in the toxicity effect produced by the different compounds.

The slope of the log-probit regression line was generally small and much smaller than that for imidacloprid. When treated by incorporation into the adult diet the compounds were much less toxic. Topical treatment of the larval stage was also much less toxic but the regression line slope increased uniformly.

Some of the compounds were tested by topical application on adult house fly and were much less toxic compared to the fruit fly adults.

The slopes of the log-probit regression line were similar to those obtained by the same type of treatment used in adult fruit fly, suggesting a mechanism of action similar although with less activity and some selectivity.

Contrary to the high insectividal activity found, the compounds have a very low toxicity against brine shrimps.

The high values of $LC_{50}$ are associated with steep regression lines.

It can be concluded that these compounds show a very low toxicity towards this type of organisms in saline medium, not producing toxicity in these ecosystems.

In the test of spraying the compounds on leaves infested with adult white flies the compounds of Examples 4 and 9 were found to be promising for activity against the white fly. These compounds also showed high toxicity against adult fruit flies.

REFERENCES

1. Haynes, L. J.; Plimmer, J. R Q. *Rev. Chem. Soc.* 1960, 14, 292-315.
2. Devon, T. K.; Scott, A. I. *Handbook of Naturally Occurring Compounds*; Academic Press: New York, 1972; Vol. II, pp. 79-175 (quoted in Ref. 8).
3. Marshall, P. G. In *Chemistry of Carbon Compounds*; Rodd, E. H., Ed.; Elsevier: New York, 1970; Vol. II D, Chapter 17 (quoted in Ref. 8).
4. (a) Schmitz, F. J.; Kraus, K. W.; Ciereszko, L. S.; Sifford, D. H.; Weinheimer, A. J. *Tetrahedron Lett.* 1966, 7, 97-104; (b) Cimino, G.; De Stefano, S.; Minale, L.; Fattorusso, E. *Tetrahedron* 1972, 28, 333-341; (c) Cafieri, F.; Fattorusso, E.; Santacroce, C.; Minale, L.; *Tetrahedron* 1972, 28, 1579-1583; (d) Faulkner, D. J. *Tetrahedron Lett.* 1973, 14, 3821-3822; (e) Rothberg, I.; Shubiak, P. *Tetrahedron Lett.* 1975, 16, 769-722; (f) Cimino, G.; De Stefano, S.; Guerriero, A.; Minale, L. *Tetrahedron Lett.* 1975, 16, 1417-1420.
5. Ma, S; Schi, Z. ; Yu, Z. *Tetrahedron* 1999, 55, 12137-12148.
6. Larock, R. C.; Riefling, B.; Fellows, C. A. *J. Org. Chem.* 1978, 43, 131-137.
7. Brownbridge, P.; Chan, T. H. *Tetrahedron Lett.* 1980, 21, 3431-3434.
8. Cardellach, J.; Estopa, C.; Font, J.; Moreno-Mañas, M.; Ortuño, R. M.; Sachez-Ferrando, F.; Valle, S.; Vilamajo, L. *Tetrahedron* 1982, 38, 2377-2394.
9. Kotora, M.; Negishi, E. *Synthesis* 1997, 121-128.
10. Klein Gebbinck, E. A.; Stork, G. A.; Jansen, B. J. M.; of Groot, A. *Tetrahedron* 1999, 55, 11077-11094.
11. Choudhury, P. K.; Foubelo, F.; Yus, M. *Tetrahedron* 1999, 55, 10779-10788.
12. Figueredo, M.; Font, J.; Virgili, A. *Tetrahedron* 1987, 43, 1881-1886.
13. Rauter, A. P.; Ferreira, M. J.; Font, J.; Virgili, A.; Figueredo, M.; Figueiredo, J. A.; Ismael, M. I.; Canda, T. L. *J. Carbohydr. Chem.* 1995, 14, 929-948.
14. Rauter, A. P.; Figueiredo, J. A.; Ismael, M. I.; Pais, M. S.; Gonzalez, A. G.; Dias, J.; Barrera, J. B. *J. Carbohydr. Chem.* 1987, 6, 259-272.
15. Rauter, A. P.; Figueiredo, J.; Ismael, M.; Canda, T. L.; Font, J.; Figueredo, M. *Tetrahedron: Asymmetry* 2001, 12, 1131-1146.
16. Csuk, R.; Furstner, A.; Weidmann, H. *J. Chem. Soc., Chem. Commun.* 1986, 775.
17. Csuk, R.; Glänzer, B. I.; Hu, Z.; Boese, R. *Tetrahedron* 1994, 50, 1111-1124.
18. Hanessian, S.; Girard, C. *Synlett* 1994, 10, 865-867.
19. Rao, A. S. *Tetrahedron* 1983, 39, 2323-2367.
20. Garem, B. *Tetrahedron* 1978, 34, 3353-3383.
21. Rodrigues, J.; Dulcere, J. P. *Synthesis*, 1993, 1177-1202.
22. Waggins, L. F. *Nature*, 1950, 165.
23. Ohle, M.; Vargha, L. V. *J. Chem. Soc.* 1959, 2717.
24. Mitsunobu, O. *Synthesis* 1981, 1.
25. Szeja, W. *Synthesis* 1985, 983-985.
26. Kwart, H.; Hoffman, D. M. *J. Org. Chem.* 1966, 31, 419-425.
27. Gutshe, C. D. *Organic Reactions*, 1954, 8, 364.
28. Rauter, A. P.; Figueiredo, J. A.; Ismael, M. I., *Carbohydr. Res.* 1989, 188, 19-24.
29. Dax, K.; Rauter, A. P.; Stütz, A. E.; Weidmann, H., *Liebigs Ann. Chem.* 1981, 1768-1773.
30. Robertson, J. L.; Preisher, H., *Pesticide Bioassays with Arthropods*, 1992, CRC Press, Boca Raton, Fla.

The invention claimed is:

1. A method for controlling pests, the method comprising applying an effective amount to pests or their locus of one or more compounds of general formula (I')

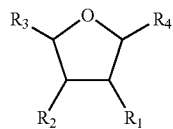
(I')

wherein
   $R_1$ and $R_2$ represent, independently from each other, hydrogen, halogen, alkoxy, substituted alkoxy or an ester group; or
   $R_1$ and $R_2$, together with the carbon atoms to which they are attached, represent an oxirane ring; or
   $R_1$ and $R_2$, taken together, represent an akylidenedioxy or substituted alkylidenedioxy group; and
   $R_3$ represents —$CH_2R_6$ (wherein $R_6$ represents an ester group), oxiranyl, or a group of formula

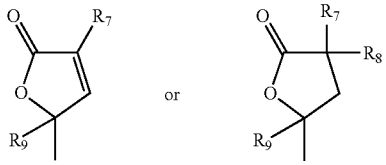

wherein
   $R_7$ represents hydrogen or alkyl,
   $R_8$ represents phenylsulfanyl, phenylselenyl, phenylsulfoxy or phenylselenoxy, and
   $R_9$ represents hydrogen, ethoxycarbonyl or carbamoyl; and
   $R_4$ represents, independently, hydrogen, alkoxy or substituted alkoxy, or
   $R_1$ and $R_4$, taken together, represent an alkylidenedioxy or a substituted alkylidenedioxy group;
wherein the pest dies as a result of contact with the compound.

2. The method according to claim 1, wherein the compound of formula (I') comprises
   $R_1$ and $R_2$ represent, independently from each other, hydrogen, alkoxy, substituted alkoxy or an ester group; or
   $R_1$ and $R_2$, together with the carbon atoms to which they are attached, represent an oxirane ring; or
   $R_1$ and $R_2$, taken together, represent an akylidenedioxy or substituted alkylidenedioxy group; and
   $R_3$ represents a group of formula

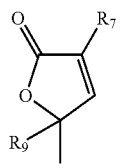

wherein
   $R_7$ represents hydrogen or alkyl, and
   $R_9$ represents hydrogen, ethoxycarbonyl or carbamoyl; and
   $R_4$ represents, independently, hydrogen, alkoxy or substituted alkoxy, or
   $R_1$ and $R_4$, taken together, represent an alkylidenedioxy or a substituted alkylidenedioxy group.

3. The method according to claim 2, wherein the compound of formula (I') comprises the formula (IA)

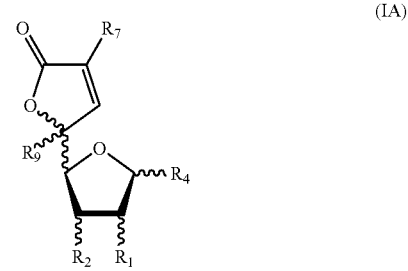
(IA)

wherein $R_1$, $R_2$, $R_4$, $R_7$ and $R_9$ have the meanings defined in claim 2.

4. The method according to claim 3, wherein $R_1$ and $R_4$, taken together, represent the isopropylidenedioxy group, $R_2$ represents benzyloxy, $R_7$ represents methyl, and $R_9$ represents hydrogen.

5. The method according to claim 4, wherein the compound is a D-gluco derivative, i.e., 3-O-benzyl-6,7-dideoxy-1,2-O-isopropylidene-7-methyl-α-D-gluco-oct-6-enofuranurono-8,5-lactone.

6. The method according to claim 4, wherein the compound is a D-alo derivative, i.e., 3-O-benzyl-6,7-dideoxy-1,2-O-isopropylidene-7-methyl-α-D-alo-oct-6-enofuranurono-8,5-lactone.

7. The method according to claim 3, wherein $R_1$ and $R_4$, taken together, represent an isopropylidenedioxy group, $R_2$ represents benzyloxy, and $R_7$ and $R_9$ represent hydrogen.

8. The method according to claim 7, wherein the compound is a D-alo derivative.

9. The method according to claim 8, wherein the compound is 3-O-benzyl-6,7-dideoxy-1,2-O-isopropylidene-α-D-alo-oct-6-enofuran-urono-8,5-lactone.

10. The method according to claim 7, wherein the compound is a D-gluco derivative.

11. The method of claim 10, wherein the compound is 3-O-benzyl-6,7-dideoxy-1,2-O-isopropylidene-α-D-gluco-oct-6-enofuranurono-8,5-lactone.

12. The method according to claim 1, wherein, in the compound of formula (I')
   $R_1$ and $R_2$ represent, independently from each other, hydrogen, alkoxy or substituted alkoxy; or
   $R_1$ and $R_2$, together with the carbon atoms to which they are attached, represent an oxirane ring; or
   $R_1$ and $R_2$, taken together, represent an akylidenedioxy or substituted alkylidenedioxy group; and $R_3$ represents a group of formula

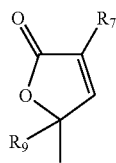

wherein $R_7$ represents hydrogen or alkyl, $R_8$ represents phenylsulfanyl, phenylselenyl, phenylsulfoxy or phenylselenoxy, and $R_9$ represents hydrogen, ethoxycarbonyl or carbamoyl; and $R_4$ represents, independently, hydrogen, alkoxy or substituted alkoxy, or $R_1$ and $R_4$, taken together, represent an alkylidenedioxy or a substituted alkylidenedioxy group.

13. The method according to claim 12, wherein the compound of formula (I'), comprises the formula (IC)

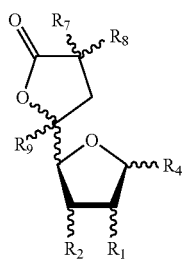

(IC)

wherein $R_1$, $R_2$, $R_4$, $R_7$, $R_8$ and $R_9$ have the meanings defined in claim 12.

14. The method according to claim 13, wherein $R_1$ and $R_2$, together with the carbon atoms to which they are attached, form an oxirane ring, $R_4$ represents methoxy, $R_7$ represents methyl, $R_8$ represents phenylselenyl and $R_9$ represents hydrogen.

15. The method according to claim 14, wherein the compound is a 2,3-anhydrous-β-L-gulo derivative.

16. The method according to claim 15, wherein the compound is methyl (7R)- and methyl (7S)-2,3-anhydro-6,7-dideoxy-7-phenylselenyl-7-methyl-β-L-gulo-octofuranurono-8,5-lactone.

17. The method according to claim 14, wherein $R_1$ and $R_4$, taken together, form an isopropylidenedioxy group, $R_2$ represents hydrogen, $R_7$ represents methyl, $R_8$ represents phenylselenyl and $R_9$ represents hydrogen.

18. The method according to claim 17, wherein the compound is a D-ribo derivative, i.e., (7R)- and (7S)-3,6,7-trideoxy-7-phenylselenyl-1,2-O-isopropylidene-7-methyl-α-D-ribo-octofuranurono-8,5-lactone.

19. The method according to claim 13, wherein $R_1$ and $R_4$, taken together, form an isopropylidenedioxy group, $R_2$ represents benzyloxy, $R_7$ represents methyl, $R_8$ represents phenylselenyl and $R_9$ represents hydrogen.

20. The method according to claim 19, wherein the compound is a D-gluco derivative, i.e., (7R)- and (7S)-3-O-benzyl-6,7-dideoxy-7-phenylselenyl-1,2-O-iso-propylidene-7-methyl-α-D-gluco-octofuranurono-8,5-lactone.

21. The method according to claim 1, wherein, in the compound of formula (I'), $R_1$ and $R_2$, together with the carbon atoms to which they are attached, represent an oxirane ring; and $R_3$ represents oxiranyl; and $R_4$ represents alkoxy or substituted alkoxy.

22. The method according to claim 21, wherein the compound of formula (I'), comprises formula (ID)

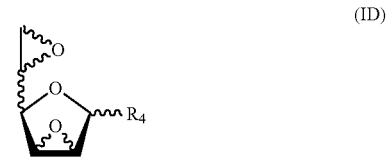

(ID)

wherein $R_4$ has the meaning defined in claim 21.

23. The method according to claim 22, wherein $R_4$ represents methoxy.

24. The method according to claim 23, wherein the compound is a 2,3;5,6-dianhydro-β-L-gulo, i.e., methyl 2,3;5,6-di-anhydro-β-L-gulo-furanoside.

25. The method according to claim 1, wherein, in the compound of formula (I'), $R_1$ and $R_2$ represent, independently from each other, hydrogen, alkoxy or substituted alkoxy; or $R_1$ and $R_2$, taken together, represent an alkylidenedioxy or substituted alkylidenedioxy group; and $R_3$ represents oxiranyl; and $R_4$ represents, independently, hydrogen, alkoxy or substituted alkoxy, or $R_1$ and $R_4$, taken together, represent an alkylidenedioxy or substituted alkylidene-dioxy group.

26. The method according to claim 25, wherein the compound of formula (I) presents formula (IE)

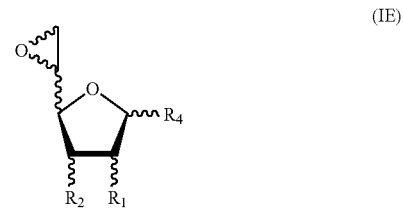

(IE)

wherein $R_1$, $R_2$ and $R_1$ have the meanings defined in claim 25.

27. The method of claim 1, wherein the pests are arthropods.

28. The method according to claim 27, wherein the arthropods are insects.

29. The method according to claim 28, wherein the insects are fruit fly (*Drosophila melanogaster*), housefly (*Musca domestica*) and whitefly (*Trialeurodes vaporarium*).

* * * * *